US010238586B2

(12) United States Patent
Shields, IV et al.

(10) Patent No.: US 10,238,586 B2
(45) Date of Patent: Mar. 26, 2019

(54) COMPOSITIONS, SYSTEMS AND METHODS FOR THE ENCAPSULATION AND DELIVERY OF A SUBSTANCE

(71) Applicant: Duke University, Durham, NC (US)

(72) Inventors: Charles W. Shields, IV, Durham, NC (US); Gabriel P. Lopez, Durham, NC (US); Nick Kirby, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/492,786

(22) Filed: Apr. 20, 2017

(65) Prior Publication Data
US 2017/0304162 A1    Oct. 26, 2017

Related U.S. Application Data

(63) Continuation of application No. 62/325,117, filed on Apr. 20, 2016.

(51) Int. Cl.
*A61K 8/11* (2006.01)
*A61K 8/892* (2006.01)
(Continued)

(52) U.S. Cl.
CPC .............. *A61K 8/11* (2013.01); *A61K 8/342* (2013.01); *A61K 8/671* (2013.01); *A61K 8/891* (2013.01);
(Continued)

(58) Field of Classification Search
None
See application file for complete search history.

(56) References Cited

U.S. PATENT DOCUMENTS 5,851,538 A    12/1998 Froix et al.
6,337,089 B1    1/2002 Yoshioka et al.
(Continued)

FOREIGN PATENT DOCUMENTS

CN    103417975 A    12/2013
EP    1742620 B1    12/2012

OTHER PUBLICATIONS

Shields (Shields, C.W., IV, Nucleation and Growth Synthesis of Siloxane Gels to Form Functional, Monodisperse, and Acoustically Programmable Particles, Angew. Chem. Int. Ed., 53 (2014) pp. 8070-8073; on Sep. 12, 2017 IDS) (Year: 2014).*

(Continued)

*Primary Examiner* — Bethany P Barham
*Assistant Examiner* — Dominic Lazaro

(57) ABSTRACT

A composition and method is provided for synthesizing silicone particles with narrow size distributions and tunable degrees of crosslinking for encapsulation of an active ingredient or multiple active ingredients in the matrix of the particles for controlled release. The method comprises agitating at least one type of silane monomer having two, three or four siloxane bonds in an acidic aqueous solution under conditions sufficient to allow for hydrolysis of the monomers, adding a catalyst and a solution comprising a co-solvent and the active ingredient(s) to the acidic aqueous solution, and continuing to agitate the combined solution to allow for a condensation reaction and formation of silicone particles with a narrow size distribution encapsulating at least a portion of the active ingredient(s). The tunable degree of crosslink density of the particles formed is based on the ratios of the monomers used, which enables controlled release of the active ingredient(s) from the particles.

17 Claims, 12 Drawing Sheets

(51) Int. Cl.
*A61Q 19/08* (2006.01)
*A61K 8/34* (2006.01)
*A61K 8/891* (2006.01)
*A61Q 19/00* (2006.01)
*A61K 8/67* (2006.01)
*A61K 8/893* (2006.01)

(52) U.S. Cl.
CPC .............. *A61K 8/892* (2013.01); *A61K 8/893* (2013.01); *A61Q 19/00* (2013.01); *A61Q 19/08* (2013.01); *A61K 2800/652* (2013.01); *A61K 2800/654* (2013.01)

(56) References Cited

U.S. PATENT DOCUMENTS

| | | | |
|---|---|---|---|
| 2003/0232091 A1 | 12/2003 | Shefer et al. | |
| 2008/0317795 A1* | 12/2008 | Traynor | A61K 8/062 424/401 |
| 2015/0196515 A1 | 7/2015 | Aliyar et al. | |

OTHER PUBLICATIONS

Supporting Information (http://dx.doi.org/10.1002/anie.201402471, dated 2014, accessed on Oct. 29, 2017). (Year: 2014).*
Vogel, R., et al., Fluorescent organosilica micro- and nanoparticles with controllable size, Journal of Colloid and Interface Science, 310 (2007) pp. 144-150. (Year: 2007).*
Goller, G.I., et al., Inorganic "silicone oil" microgels, Colloids and Surfaces A: Physicochemical and Engineering Aspects, 123-124 (1997) pp. 183-193. (Year: 1997).*
Shields IV, C. Wyatt, et al., "Nucleation and growth synthesis of siloxane gels to form functional, monodisperse, and acoustically programmable particles," Angewandte Chemie International Edition, 2014, vol. 53, No. 31, pp. 8070-8073; and supporting information see p. 8070, right column, lines 11-12; supporting information, p. 1, lines 3-4 and 16-17; and supporting figures 1, 2.
PCT, International Search Report and Written Opinion in International application No. PCT/US2017/028642 dated Aug. 3, 2017.

* cited by examiner

Cross-linking decreases

COMPOSITIONS, SYSTEMS AND METHODS FOR THE ENCAPSULATION AND DELIVERY OF A SUBSTANCE

RELATED APPLICATIONS

This application claims priority to U.S. Provisional Patent Application No. 62/325,117 filed on Apr. 20, 2016, which is incorporated by reference herein in its entirety.

TECHNICAL FIELD

The present disclosure relates to compositions, systems and methods for encapsulation and delivery of a substance. More particularly, it relates to compositions comprising silicone particles with a narrow size distribution for encapsulating active ingredients for controlled release delivery of the active ingredients in, for example, topical formulations.

BACKGROUND

There is a growing need to stabilize, protect and control the release of various substances, such as active ingredients that may be unstable, hydrophobic, volatile and/or toxic at high concentrations or sensitive to breakdown in different environmental conditions. Many of these active ingredients have useful or beneficial effects, for example, the anti-aging and anti-acne effects of retinol, which is used in formulations primarily intended for cosmetic use. For topical applications, retinol is typically formulated into creams, ointments, oils and the like. In such formulations, however, retinol can rapidly degrade and lose activity. In addition, moderate to severe skin irritation frequently results from the use of the formulations with retinol at high concentrations. This irritation is due to poor control over the dosage and delivery of the active ingredient. Similar problems exist for active ingredients used in dermatology to treat various skin diseases. For example, corticosteroids used to treat psoriasis can be challenging to formulate and deliver over time, causing the end user to apply a formulation multiple times per day, which can result in adverse side effects.

Accordingly, formulations are necessary to efficaciously deliver compositions including active ingredients in creams, lotions, powders, ointments and the like. However, such compositions that include the active ingredients are often difficult to formulate. Therefore, highly complex and intricate encapsulation methods have been developed to incorporate these substances into final product formulations. As an example, many delivery systems in the dermatological or personal care space use a core-shell encapsulation approach. However, this approach results in compositions that release their payload in the form of a bolus. Other existing solutions utilize highly complex, multi-stage processes to encapsulate the active ingredients that are difficult to scale in a technologically feasible or economically viable fashion.

For the foregoing reasons, there remains a need for an encapsulation material and a method for encapsulating active ingredients for use in controlled-release compositions and systems. The encapsulating material should improve the overall stability of the active ingredient, while effectively functioning as a vehicle to deliver active ingredients to a substrate without adversely affecting the chemical and physical properties of the active ingredients (i.e., to prevent the active ingredients from degradation). Ideally, the material and method will provide a system for encapsulating the particulate components for topical compositions for application to a substrate, such as the skin of a human or animal. The properties of the encapsulating material should be tunable so that, for example, the density, compressibility, size, size distribution and crosslink density are precisely controlled to provide the proper protection and release performance for a given application. Finally, the encapsulating material should be readily scalable to produce large quantities of material in a convenient and cost-effective manner.

SUMMARY

A method is provided for making silicone particles with narrow size distributions and tunable degrees of crosslinking for encapsulation of an active ingredient in the matrix of the particles for controlled release of the active ingredient. The method comprises the steps of agitating at least one type of silane monomer having two, three or four siloxane bonds in an acidic aqueous solution under conditions sufficient to allow for hydrolysis of the monomers and adding a catalyst to the acidic aqueous solution. A solution comprising a co-solvent and an active ingredient is also added to the acidic aqueous solution. The combined solution is agitated to allow for a condensation reaction and formation of silicone particles with a narrow size distribution encapsulating at least a portion of the active ingredient. The tunable degree of crosslink density of the particles formed is based on the ratios of the monomers used.

The method may further comprise the step of removing a majority of the polymers, gels and large oligomers from the smaller hydrolyzed monomers and oligomers via centrifugation after the hydrolysis reaction and prior to the condensation reaction.

In one aspect, the at least one type of silane monomer comprises a conjugative group such that the group is available for covalent modification in or on the formed silicone particles. The conjugative group comprises a vinyl, carboxylate, hydroxyl, epoxide, sulfhydryl, amide, acrylate, methacrylate, thiol or amine.

In another aspect, the at least one type of silane monomer having two siloxane bonds is selected from the group of dimethoxydimethylsilane (DMODMS), vinylmethyldimethoxysilane (VMDMOS), vinylmethyldiethoxysilane (VMDEOS) and/or 3-aminopropyl (diethoxy)methylsilane (AmDEOMS).

In a further aspect, the at least one type of silane monomer having three siloxane bonds is selected from the group of trimethoxymethylsilane (TMOMS), vinyltrimethoxysilane (VTMOS), triethoxyvinylsilane (VTEOS), 3-aminopropyl trimethoxysilane (AmTMOS) and/or 3-(trimethoxysilyl)propylacrylate (AcTMOS).

In yet another aspect, the at least one type of silane monomer having four siloxane bonds is selected from the group of tetraethylorthosilicate (TEOS) and/or tetramethoxysilane (TMOS).

In a further aspect, the at least one type of silane monomer is a ratio of a silane monomer having four siloxane bonds to a silane monomer having two siloxane bonds in the range of 1:1000 to 1:2.

In a still further aspect, the at least one type of silane monomer is a ratio of a silane monomer having three siloxane bonds to a silane monomer having two siloxane bonds in the range of 1:1000 to 1000:1.

In another aspect, the at least one type of silane monomer is a ratio of a silane monomer having four siloxane bonds to a silane monomer having three siloxane bonds in the range of 1:1000 to 1:2.

In a further aspect, the at least one type of silane monomer is a ratio of a silane monomer having four siloxane bonds to a silane monomer having three siloxane bonds to a silane monomer having two siloxane bonds in the range of 1:(1 to 1000):(1 to 1000).

According to the method, the catalyst is triethylamine or ammonium hydroxide.

The particles can range in size from about 100 nm to about 50 μm primarily based on the concentration of silane monomer in the acidic aqueous solution, but also by the stir speed during the polycondensation step of the reaction and by altering the type of monomers used.

In one aspect, the active ingredient is selected from retinol, retinylacetate, retinylpalmitate, alpha-tocopherol, tocopherolacetate, tocopheryl linoleate, tocopheryl nicotinate, linoleic acid, coenzyme Q-10, resveratrol, plant extracts/essential oils, ursolic acid, oleanolic acid, oil-soluble licorice, lipoic acid, desonide, clobetasol proprionate, betamethasone diproprionate, halobetasol proprionate, fluocinonide, ketoconazole, fluconazole, itraconazole, miconazole, clotrimazole, amphotericin, tretinoin, tazarotene, benzoyl peroxide, salicylic acid, pimecrolimus, mometasone furoate, fluocinolone acetonide, diflorasone diacetate, ingenol mebutate and combinations thereof.

In another aspect, the co-solvent is an organic solvent.

The method provided herein further comprises the step of adding an antioxidant to the combined solution to allow for the silicone particles encapsulating at least a portion of the antioxidant. The antioxidant may comprise butylated hydroxytoluene (BHT).

A controlled release composition is also provided, the controlled release composition made according to the method.

A controlled release composition is provided for topical delivery of a substance to a substrate. The composition comprises particles having a narrow size distribution, the particles comprising a silicone material, and an active ingredient encapsulated within the matrix of the silicone particles.

In one aspect, the particles of the composition have an average diameter of about 100 nm to about 50 μm.

In another aspect, the active ingredient of the composition is hydrophobic, and may comprise retinol in an amount effective to promote skin repair.

Still further, the composition further comprises a vehicle to form a composition selected from the group consisting of liniments, gels, lotions, creams and ointments.

A method is provided for delivering an active ingredient to a substrate. The substance delivery method comprises the steps of providing a formulation including a controlled release composition comprising particles having a narrow size distribution, the particles comprising a silicone material, and an active ingredient encapsulated within the matrix of the particles. The substance delivery method further comprises the step of applying the formulation to the substrate to deliver the encapsulated active ingredient to the substrate. The particles of the formulation have an average diameter of about 100 nm to about 50 μm.

In one aspect, the active ingredient for use in the substance delivery method is hydrophobic. The active ingredient may comprise retinol in an amount effective to promote skin repair.

The substance delivery method may further comprise the step of providing the formulation comprising a vehicle selected from the group consisting of liniments, gels, lotions, creams and ointments.

In another aspect, the substrate comprises one of a biological surface, human body tissue and animal body tissue.

When the substrate is skin, the step of topically applying the composition to the substrate further comprises topically applying the composition to the skin to deliver the active ingredient to the skin.

In a further aspect, the substrate is selected from wood, metal, ceramic, plastic, glass or other solid material. The substrate may comprise flora.

A method is provided for delivering an active ingredient to a substrate. The active ingredient delivery method comprises the steps of providing a formulation including a controlled release composition comprising the active ingredient in the matrix of silicone particles for controlled release of the active ingredient, wherein the controlled release composition is made according to the methods as described herein. The active ingredient delivery method further comprises the step of applying the formulation to the substrate to deliver the encapsulated active ingredient to the substrate.

BRIEF DESCRIPTION OF THE DRAWINGS

For a more complete understanding of the compositions, systems and methods for encapsulation and delivery of a substance, reference should now be had to the embodiments shown in the accompanying drawings and described below. In the drawings.

DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

According to one embodiment, particles comprising a silicone material with a narrow size distribution are provided for use in a tunable, controllable, and programmable system for formulating a controlled-released composition for topical application and delivery of active ingredients to a substrate. As used herein, the term "narrow size distribution" means the silicone particles meet a threshold of variance within a preferred limit to the overall size dispersity of the particles. In one embodiment, the sizes of the particles possess a coefficient of variance of 50% or less. The particles can be synthesized from various silicone materials and combinations thereof. In some embodiments, the silicone material is selected from the group consisting of silicon alkoxide monomers or polymers, alkoxysilane monomers or polymers, other silicone derivatives with siloxane bonds. Suitable examples include, but are not limited to, tetraethyl orthosilicate, tetramethyl orthosilicate, trimethoxymethylsilane, vinyltrimethoxysilane, triethoxyvinylsilane, (3-aminopropyl)trimethoxysilane, 3-(trimethoxysilyl)propyl acrylate, dimethoxydimethylsilane, vinylmethyldiethoxysilane, dimethoxymethylvinylsilane, 3-aminopropyl (diethoxy)methylsilane, silsesquioxane, other similar types of silicon-based materials and combinations thereof.

The silicone particles may be synthesized using a sol-gel process. In one embodiment, the methods described in U.S. Pub. Appln. No. 2015/0118692 may be used to prepare the silicone particles. Other suitable methods may be used including, but not limited to, the sol-gel processes described in any disclosure relating to the sol-gel technique, such as described in WO 98/031333, WO 00/09652, WO 01/80823, WO 04/081222, WO 05/009604, WO 07/015243 and U.S. Pat. No. 8,815,291, the contents of all of which are hereby incorporated herein in their entirety.

Figure 1:
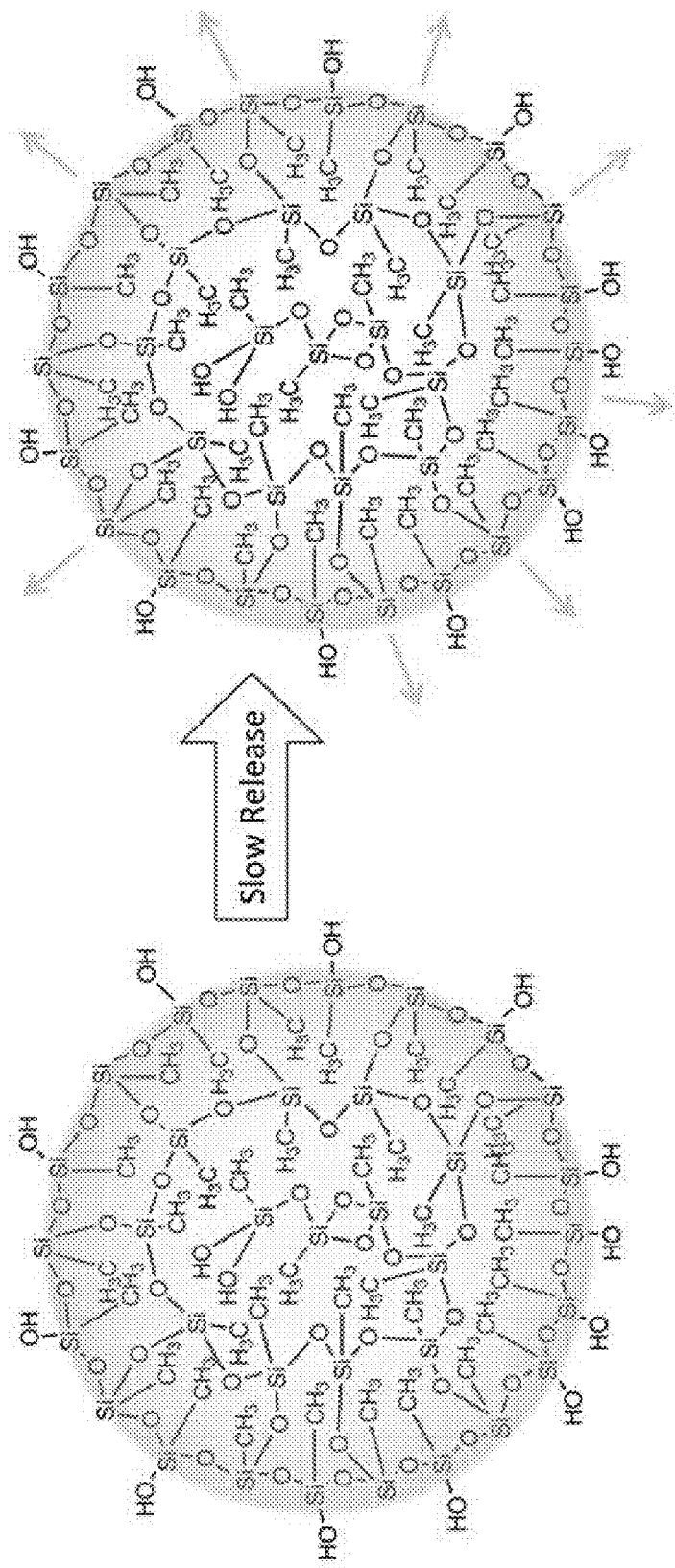
FIG. 1 is a schematic diagram showing release of encapsulated active ingredients from a silicone particle.
Figure 2:
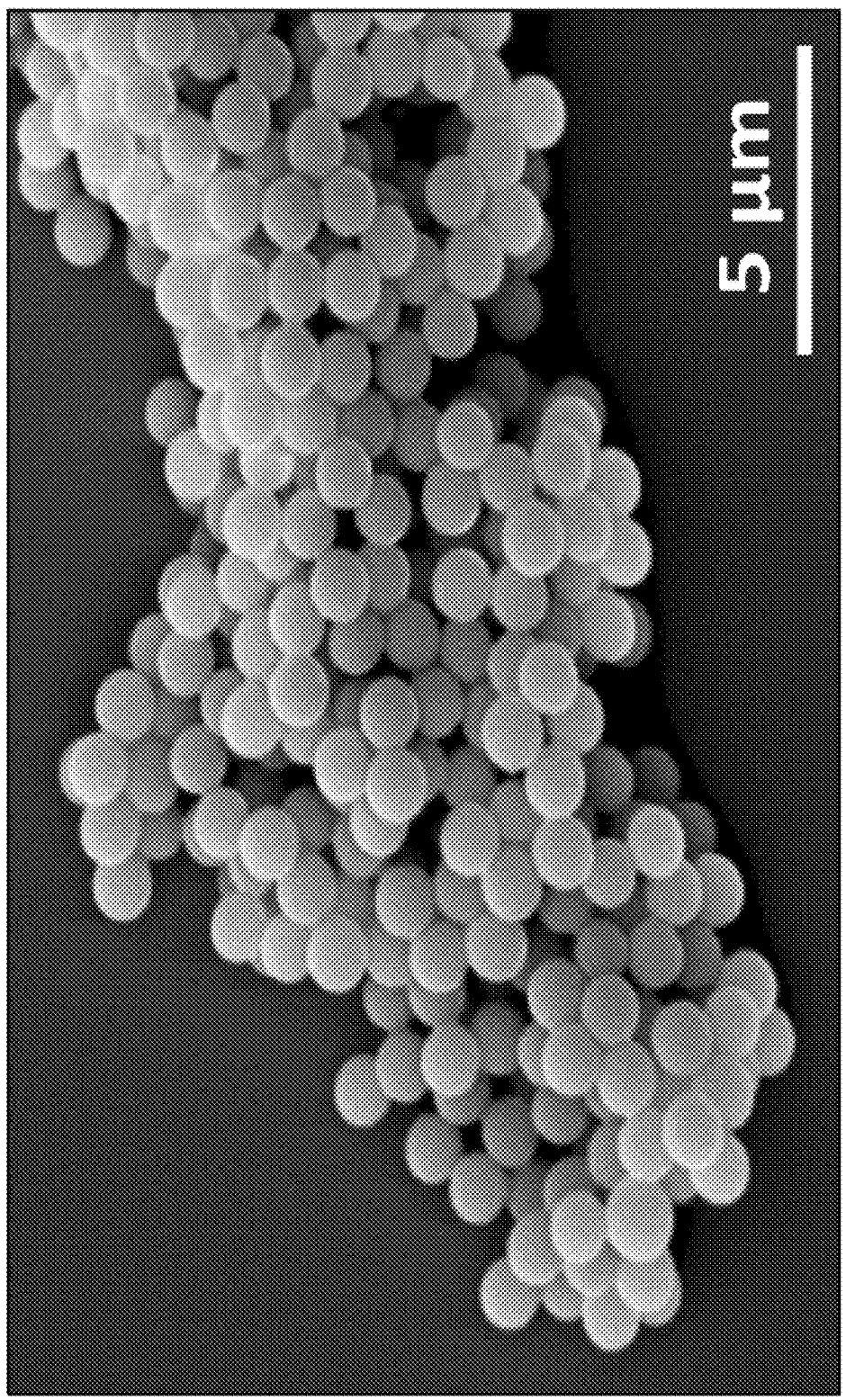
FIG. 2 is a scanning electron micrograph of silicone particles not containing an encapsulated active ingredient (scale bar is 10 μm).
Figure 3:
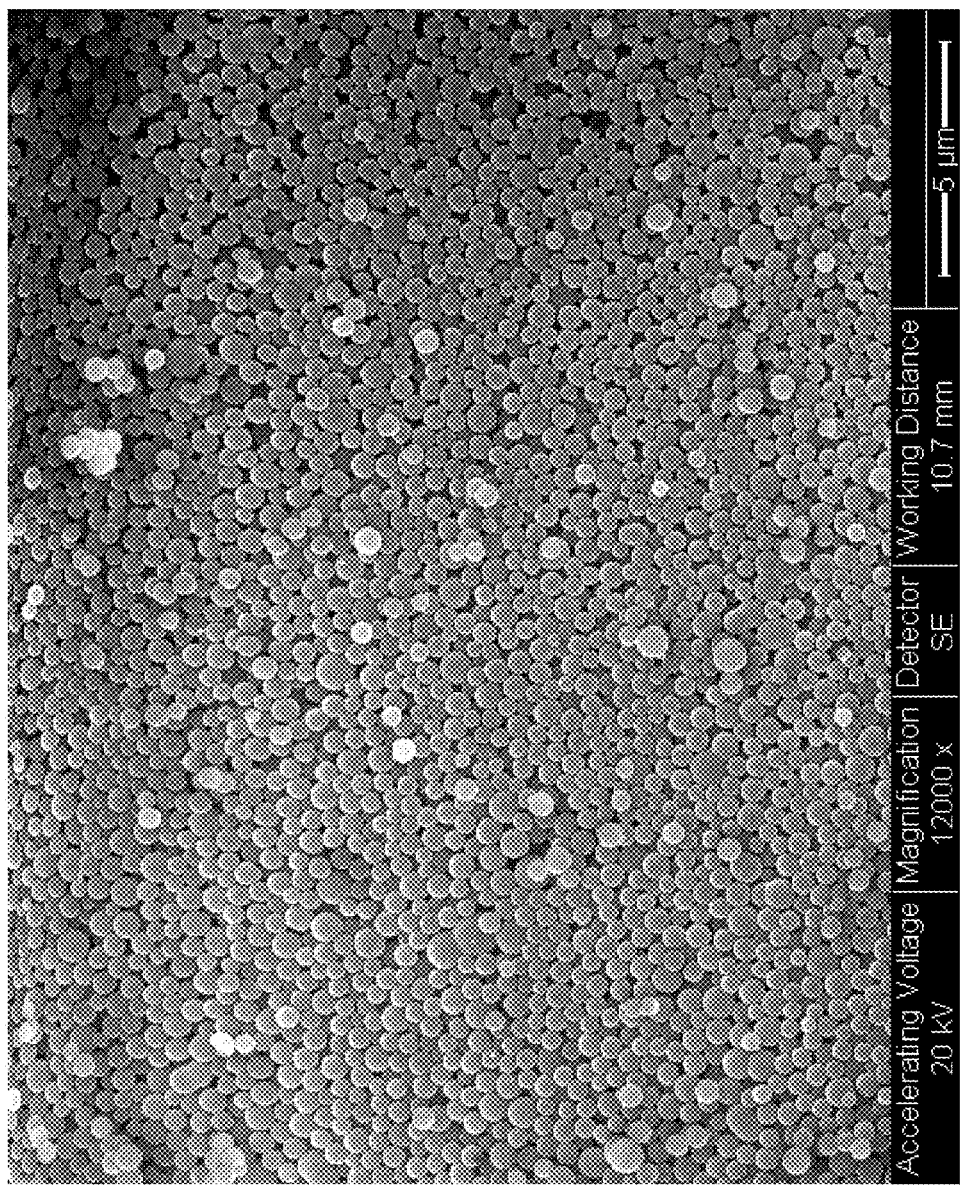
FIG. 3 is a scanning electron micrograph of silicone particles containing an encapsulated active ingredient, all-trans retinol at 10 wt. %.

The silicone particles are used for encapsulation of active ingredients for use in the controlled-release compositions (FIGS. 1-3). The controlled-release compositions, which are hereinafter simply referred to as "the compositions", include the active ingredient encapsulated in the silicone particles. The physical or chemical properties of the encapsulated active ingredients pertaining to or associated with their desired activities in the compositions are not adversely affected, while the silicone particles provide improved stability of the active ingredients.

The controlled-release compositions provide methods for delivery of the active ingredients to a substrate upon application of the composition to the substrate. Selective control of the properties of the encapsulating silicone material provides tunable controlled release of the encapsulated active ingredients. A broad range of compositions and combinations of silicone materials are suitable for the encapsulation and release of active ingredients. As a result, it is possible to adjustably control the release rate, release amount, or release profile of various substances and active ingredients from the particles by controlling, selecting, or programming the composition of the particles. For example, compliant particles (e.g., emulsions or gels with a lower crosslink density) tend to release encapsulated substances more easily likely due to increased porosity or increased compressibility, whereas stiff particles (e.g., silicones with a higher compressibility or silica) tend to retain encapsulated substances for longer durations for more long-term delivery likely due to decreased porosity or decreased compressibility. By tuning the size, chemical properties and mechanical properties of the silicone particles it is possible to control the release rate of the encapsulated active ingredient over long periods. Accordingly, a tunable, controllable and programmable silicone microsphere delivery system is possible comprising silicone particles. Additionally, since the silicone particles display a narrow size distribution and have a uniform composition throughout the structure of the particles, the release profile can be tuned to precise values over time, which is useful for active ingredients with narrow therapeutic windows, as an example.

The active ingredients useful for the present compositions can be any hydrophobic active agent that are commonly used, for example, in topical cosmetic or pharmaceutical compositions, which include, but are not limited to, desonide, clobetasol proprionate, betamethasone diproprionate, halobetasol proprionate, fluocinonide, ketoconazole, fluconazole, itraconazole, miconazole, clotrimazole, amphotericin, tretinoin, tazarotene, retinol, benzoyl peroxide, salicylic acid, pimecrolimus, mometasone furoate, fluocinolone acetonide, diflorasone diacetate and ingenol mebutate.

A co-solvent is used to facilitate the integration of hydrophobic active ingredients into the aqueous phase where the particles are grown, such that the particles encapsulate the active ingredient as the reaction proceeds. First, a co-solvent (i.e., an organic solvent such as acetone, isopropyl alcohol or ethanol) is used to dissolve the active ingredient prior to dispersing in the reaction medium. The efficiency of encapsulation is dependent on the concentration of co-solvent. As active ingredients in lower concentrations of co-solvent tend to generate precipitates when added to the aqueous phase, thus reducing the efficiency of encapsulation; however, higher concentrations of co-solvent tend to stabilize the active ingredient in the aqueous phase, thus increasing the energetic penalty for active ingredients to embed in the particles. The type of co-solvent and its concentration directly affects the encapsulation efficiency of the active ingredient for a given particle composition.

The silicone particles and active ingredients are used either alone or as dispersions in a suitable vehicle in a form resembling those of conventional skin preparations such as liniments, gels, lotions, creams or ointments. Furthermore, multiple silicone particle types containing different active ingredients can be used in a single formulation to allow for different release rates of each active ingredient in the same formulation. Optionally, other active or inert substances in solid form or dissolved in a suitable solvent, may be used as other formulating components. The other components may include, for example, binders. The binder can be included in the formulation to facilitate or maintain the controlled release particles in a predetermined form including, e.g., tablet, pellet or brick. Examples of suitable binders include polymers, starches, gums and clays.

The controlled-release compositions are useful in personal care products, topical pharmaceutical products, textiles, auto care products and laundry products for the delivery of active ingredients. The personal care products include cosmetics compositions for topical application to a substrate. The substrate is typically a biological surface, human or animal body tissue. More specific substrates include, but are not limited to, skin, hair, mucous membrane, tooth, nails and eyes.

The controlled-release composition is typically applied for topical therapy, such as to treat damaged or diseased skin, and wound care, such as to treat cuts, burns, and the like, which provides a method for continuous delivery of the active ingredients to the skin site. The controlled-release compositions may also be applied in various transdermal, pharmaceutical, veterinary and oral health care applications. The compositions can be protected with a secondary film, dressing or patch, or the compositions can be part of a more complex construction such as a transdermal patch or wound dressing.

The controlled-release compositions including active ingredients encapsulated in silicone particles are prepared in a process comprising the steps of synthesizing the particles by nucleation and growth. A method for encapsulating the active ingredients in the particles comprises the steps of dissolving the active ingredient into a pre-polymer, polymer or co-solvent and adding the solution to the particle reaction prior to, or soon after initiating, the growth step of the particle reaction. This allows the active ingredient to be physically incorporated throughout the silicone particles as the particles are formed in solution. In a further aspect, the encapsulation method further comprises the step of incorporating various additional substances into the particles before they are synthesized via co-dissolution of the additional substances in a prepolymer, polymer or co-solvent or after they are synthesized by co-incubation and diffusion.

The compositions, systems and methods for encapsulation and delivery of a substance as described herein have many advantages, including a scalable encapsulation system for providing exceptional control over particle size and the resulting extended release of active ingredients (see, e.g., Examples 1-6 and FIGS. 4-12 herein below). Because the silicone materials used to make the particles are diverse, a user can use special blends of the monomers or polymers to provide exceptional control over the morphology of the particles (e.g., density, compressibility, stiffness, crosslink density) and, subsequently, the encapsulation and release profile of the active ingredients over time. The encapsulation system is particularly applicable to the personal care and dermatological industries, but may also be relevant to paints, inks, coatings, foods, agricultural or other industrial applications. For instance, a formulation containing the encapsulation system can be used as a coating for substrates including, but not limited to, woods, metals, ceramics, plastics, glasses or other solid materials. A formulation containing the encapsulation system (e.g., encapsulated pesticides) could be used as an agricultural product to be applied to substrates including, but not limited to, household items, soils, plants, food, food derivatives or other solid materials.

EXAMPLES

The following examples are presented by way of illustration and not by way of limitation.

Figures 4A, 4B:
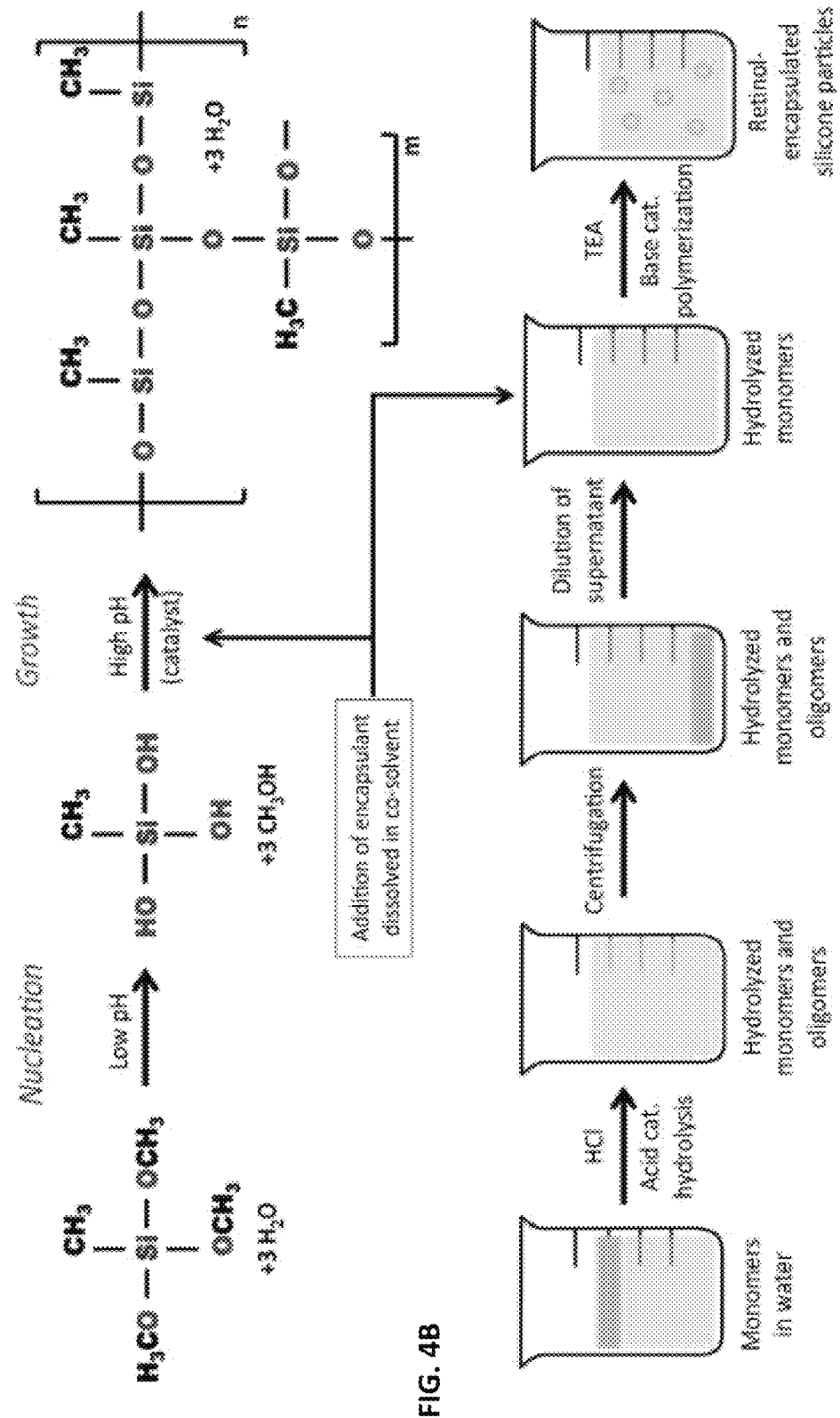
FIG. 4A shows a chemical schematic diagram of an embodiment of a method for synthesis of silicone particles and concurrent encapsulation of active ingredients.
FIG. 4B shows a schematic diagram of an embodiment of a method for synthesis of silicone particles and concurrent encapsulation of active ingredients.

Example 1. Protocol for Synthesizing Silicone Particles with an Encapsulated Retinol Payload (FIG. 4)

TABLE I

Preparation of retinol aliquots

| Particle type | Only TMOMS | 1:24 TMOS:DMODMS | 1:96 TMOS:DMODMS |
|---|---|---|---|
| Mass retinol (mg) | 35.4 | 8.97 | 2.55 |
| Mass BHT (mg) | 2.36 | 0.598 | 0.170 |
| Volume ethanol (mL) | 1 | 0.250 | 0.072 |

Step 1. Each appropriate amount of retinol was independently weighed and placed in an Eppendorf tube for a given particle composition according to Table I above.

Step 2. Butylated hydroxytoluene (BHT), an anti-oxidant, was weighed (4 mg) and placed in a separate Eppendorf tube.

Step 3. The 4 mg BHT was dissolved in 5 µL of acetone.

Step 4. An amount of the BHT/acetone solution was distributed to each of the retinol vials for a 1:15 ratio of BHT:retinol by weight.

E.g., If 4 mg of BHT is weighed and 50 µL of acetone is added, then the volume added to the TMOMS vial would be (2.36 mg/4 mg)*(50 µL)=29.5 µL Step 5. An appropriate volume of ethanol was added to the Eppendorf tube(s).

Figure 5A:
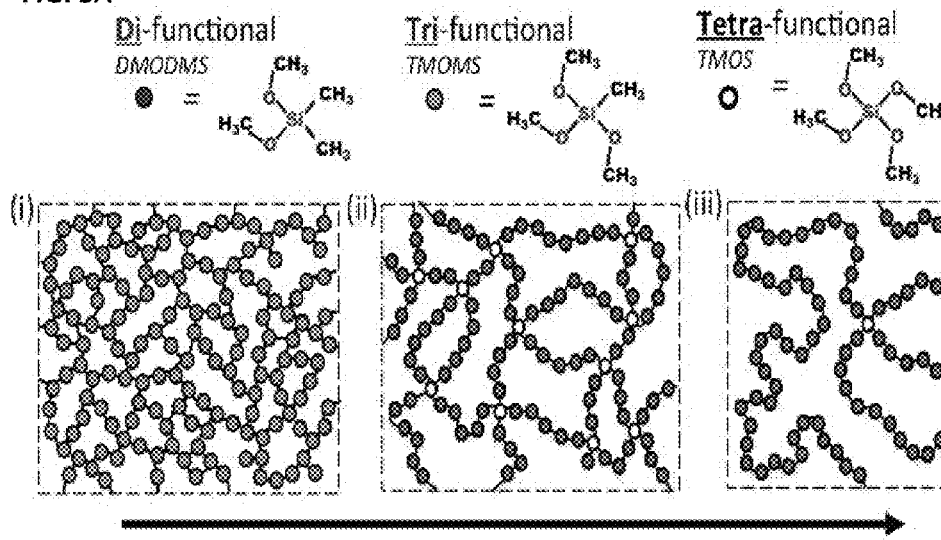
FIG. 5A is a schematic showing efficiency of encapsulation of retinol into silicone particles synthesized from various molar ratios of: (i) di-functional DMODMS, (ii) tri-functional TMOMS, and (iii) tetra-functional TMOS.
Figure 5B:
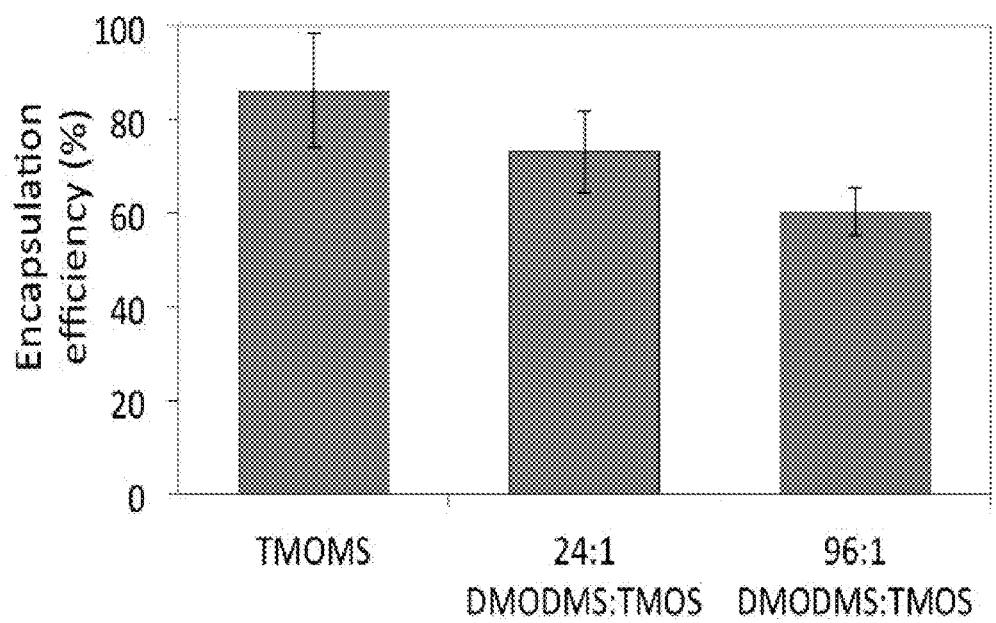
FIG. 5B is a bar graph showing efficiency of encapsulation of retinol into silicone particles synthesized from various molar ratios of TMOMS, DMODMS, and TMOS.
Figure 6:
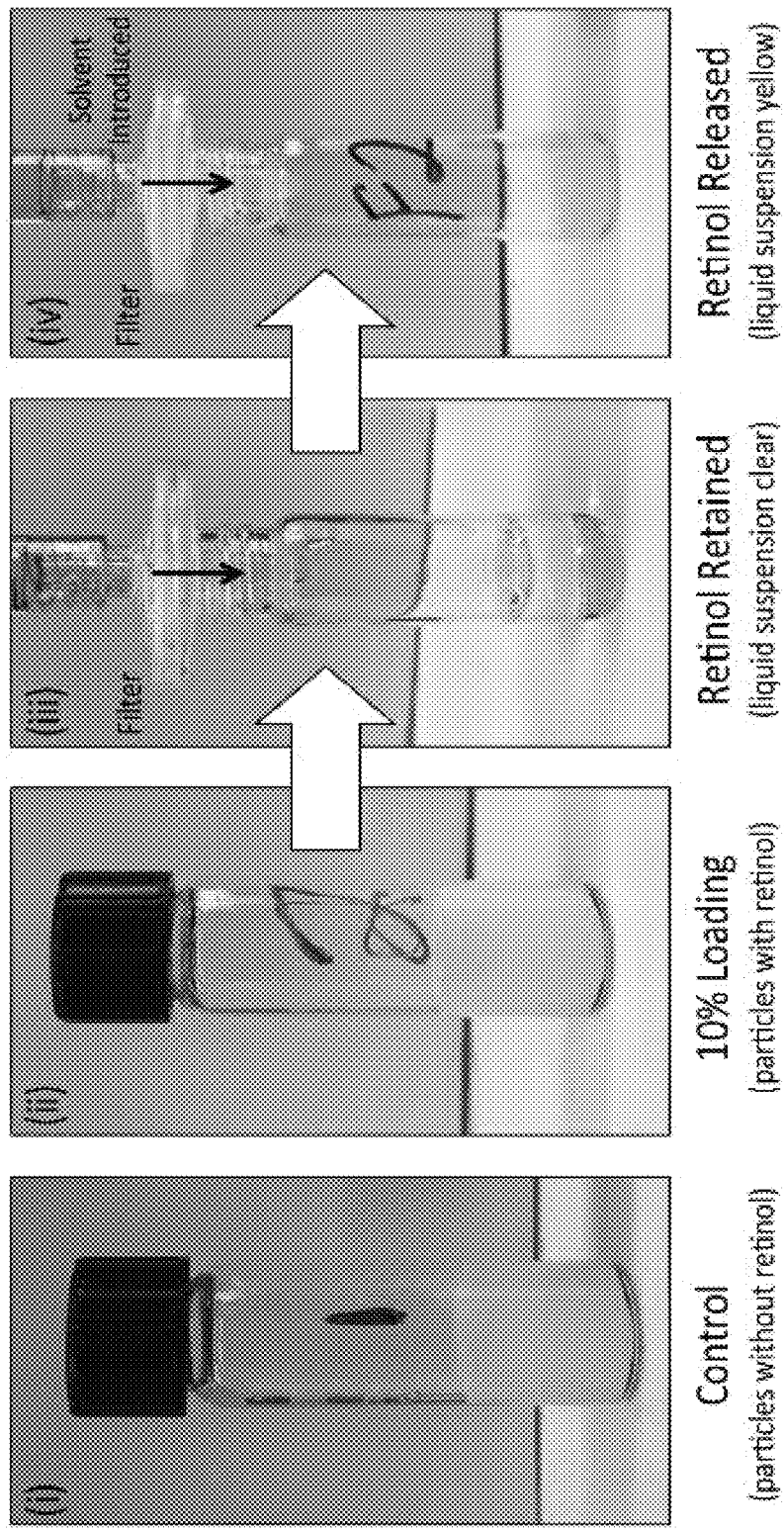
FIG. 6 shows the burst release of retinol from silicone particles in an aqueous suspension.
Figure 7:
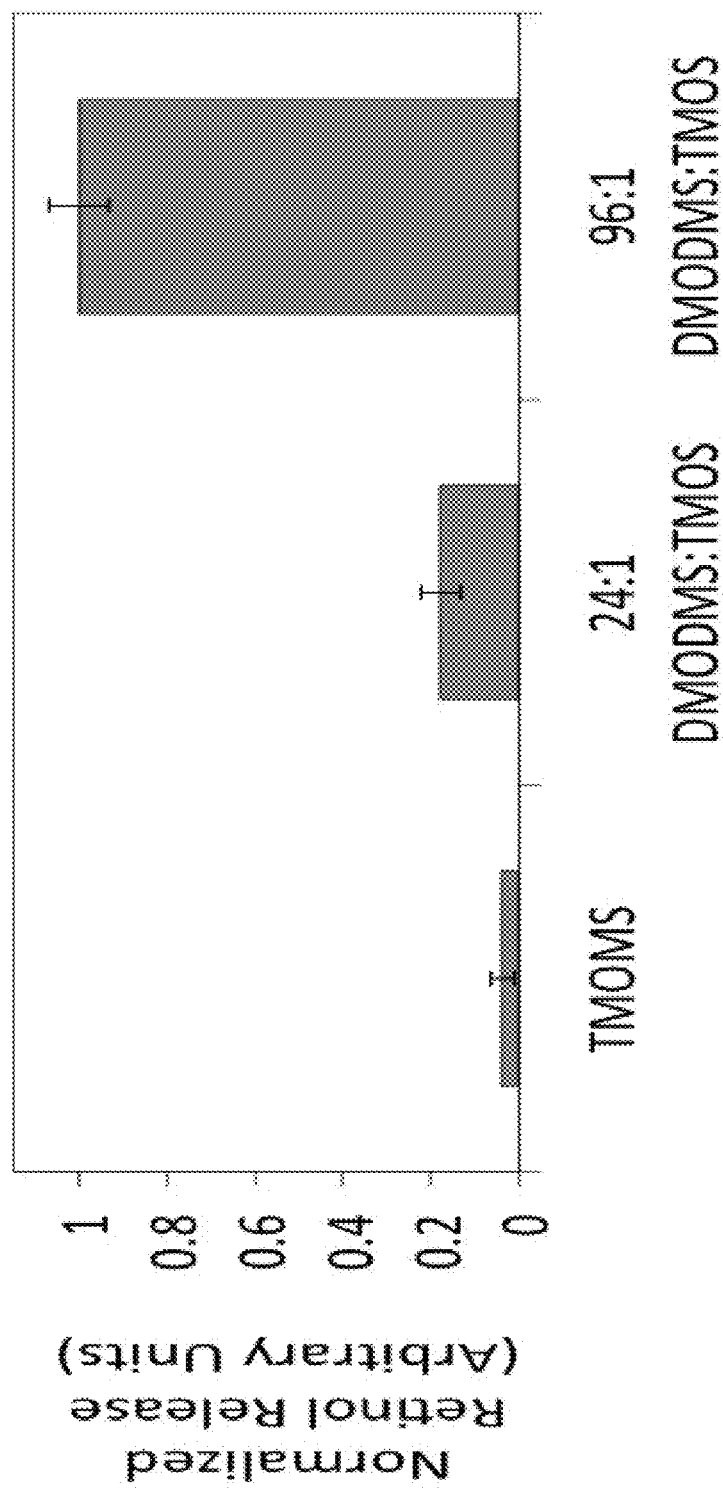
FIG. 7 is a bar graph showing controlled release of retinol from silicone particles of various compositions.

II. Preparation of Particles (FIGS. 5A and 5B)

| Particle Type | TMOMS | 1:24 TMOS:DMODMS | 1:96 TMOS:DMODMS |
|---|---|---|---|
| TMOMS (mL) | 1 | 0 | 0 |
| DMODMS (mL) | 0 | 0.957 | 0.989 |
| TMOS (mL) | 0 | 0.0435 | 0.0112 |
| Stir Time (min) | 15 | 60 | 60 |

Step 1. 219.5 µL of 0.1 M hydrochloric acid (HCl) was added to 10 mL H$_2$O and is mixed. Note, 10 mL of 0.1 M HCl (pH=1) was prepared by adding 83.3 µL of 37% HCl to 9.917 mL deionized H$_2$O.

Step 2. 1 mL of trimethoxymethylsilane (TMOMS) was added to the solution in Step 1 to make particles synthesized from TMOMS. Alternatively, 11.2 µL tetramethyl orthosilicate (TMOS) and 988.6 µL dimethoxydimethylsilane (DMODMS) was added to the solution in Step 1 for a 1:96 molar ratio of TMOS:DMODMS. Further, a 43.5 µL TMOS and 956.5 µL DMODMS was added to the solution in Step 1 for a 1:24 molar ratio of TMOS:DMODMS.

Step 3. The mixtures were stirred at 500 rpm for 90 min.

Step 4. The mixtures were centrifuged at 2000×g for 5 min.

Step 5. 7.5 mL of supernatant was extracted from mixtures and added to new vials.

Step 6. 7.5 mL of 3.1×10$^{-4}$ M HCl was added to the supernatant in the vials. Note, 7.5 mL of 3.16×10$^{-4}$ M was prepared by adding 23.7 µL 0.1 M HCl to 7.476 mL DI H$_2$O.

Step 7. 15 µL of a catalyst, triethylamine (TEA), was added to supernatant-acidic water solution.

Step 8. The solution was then stirred at 500 rpm.

Step 9. After 3-5 min of polycondensation, retinol/BHT solution was added to the vial.

Step 10. Stirring was continued for allotted time: (i) 15 min for solutions containing only TMOS monomers, and (ii) 60 min for solutions containing a 1:24 or 1:96 molar ratio of TMOS:DMODMS.

Example 2. Methods to Measure Encapsulation Efficiency

Figure 12A:
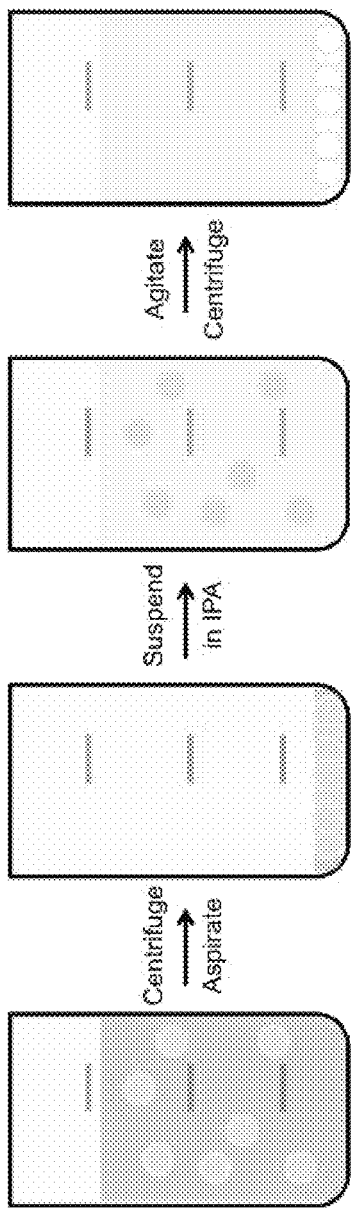
FIG. 12A shows a schematic of a "Solvent Release (SR)" method for measuring the encapsulation efficiency of hydrophobic active ingredients into the silicone particles by extracting the active ingredient via washing and diluting the solution with a solvent (e.g., isopropyl alcohol, IPA).
Figure 12B:
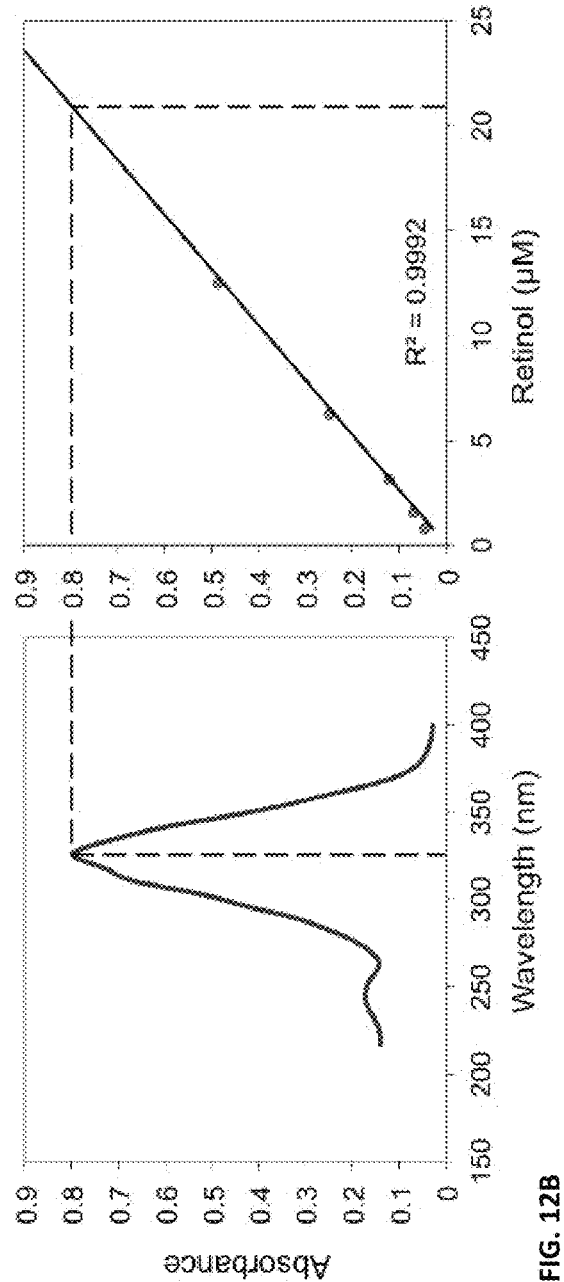
FIG. 12B shows quantification using UV-Vis spectroscopy for the "Solvent Release (SR)" method shown in FIG. 12A where the absorbance values of solutions containing retinol are used to calculate the concentration, and thus the mass, of encapsulated retinol following Beer-Lambert's Law.

Encapsulation efficiency of retinol in the silicone particles was determined using an assay referred to as a "Solvent Release (SR) Method". Referring to FIG. 12, after encapsulating retinol into the silicone particles according to Example 1, the solution was centrifuged, the particles were reconstituted in isopropyl alcohol (IPA), and the particles were vigorously agitated to expel the retinol. The solution was then centrifuged again to force the particles into a pellet to allow for the collection of the supernatant.

The absorbance spectrum of the solution was immediately measured using UV-Vis spectroscopy, whereby the concentration of retinol was determined via Beer-Lambert's Law. Notably, the amount of retinol remaining in the reaction solution was not simply measured. The SR method yields a more conservative estimate because any retinol measured by this approach is retinol that was definitively encapsulated within the particles. The SR method also provides information about the stability of retinol encapsulated within the particles since any retinol that oxidizes while in the particle is indicated by a peak shift away from 325 nm. Thus, the SR method yields meaningful information about the stability of some types of encapsulated active ingredients, for example, retinol. Other methods, such as LC-MS, should be used for active ingredients that do not absorb light in the range of conventional UV-Vis spectrophotometers.

Figure 8:
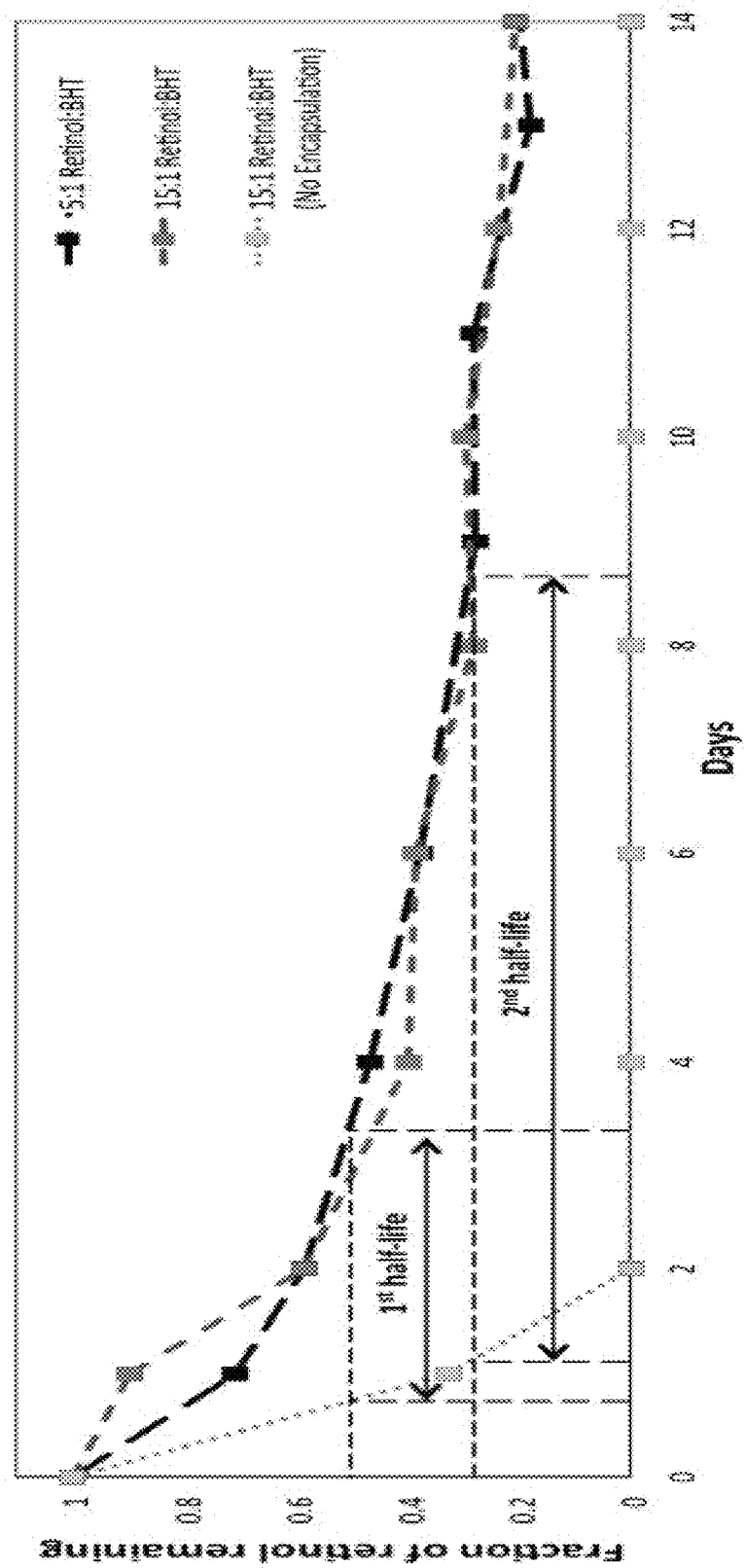
FIG. 8 shows the stability of retinol encapsulated in silicone particles suspended in water and heated to 45° C. over 14 days compared to non-encapsulated retinol under the same conditions with different ratios of butylated hydroxytoluene (BHT) by weight.
Figures 9A, 9B:
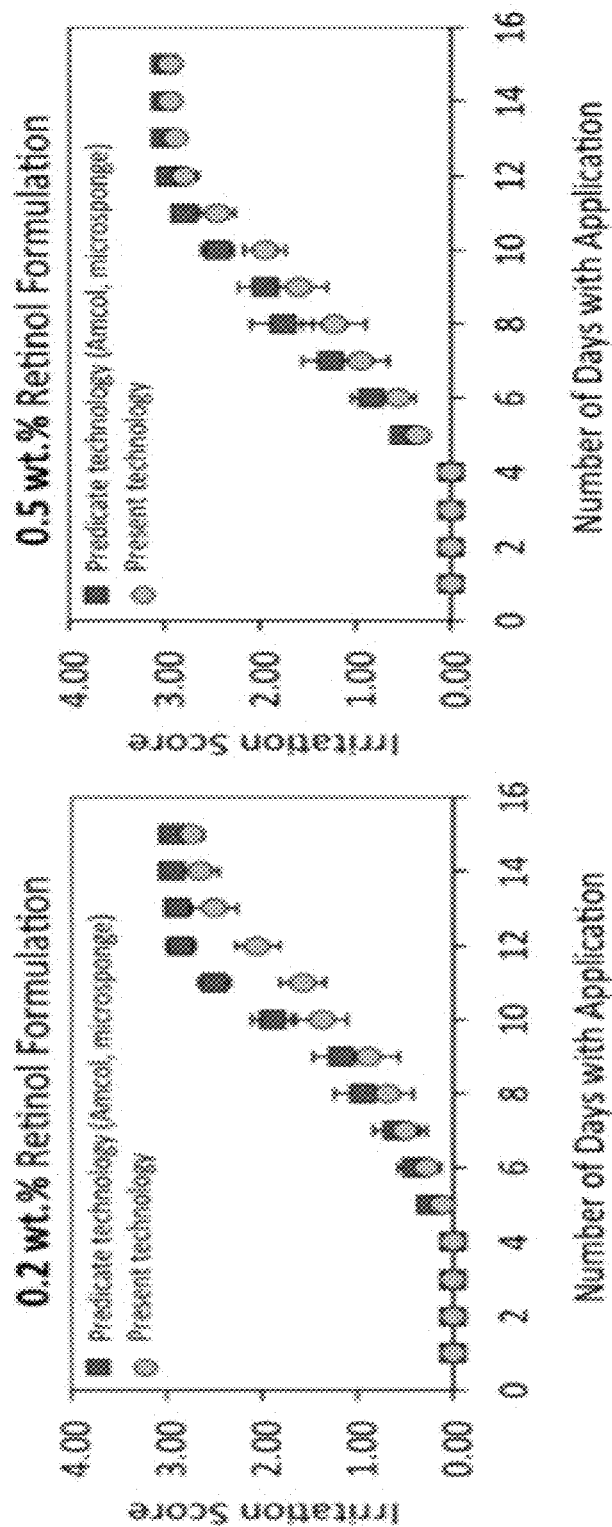
FIG. 9A shows irritation scores of a 0.2 wt % retinol formulation prepared as described in Example 4 below throughout a three-week occlusive patch test as compared to identical formulations containing a predicate microencapsulation technology, the Microsponge by Amcol.
FIG. 9B shows irritation scores of a 0.5 wt % retinol formulation prepared as described in Example 4 below throughout a three-week occlusive patch test as compared to identical formulations containing a predicate microencapsulation technology, the Microsponge by Amcol.
Figure 10B:
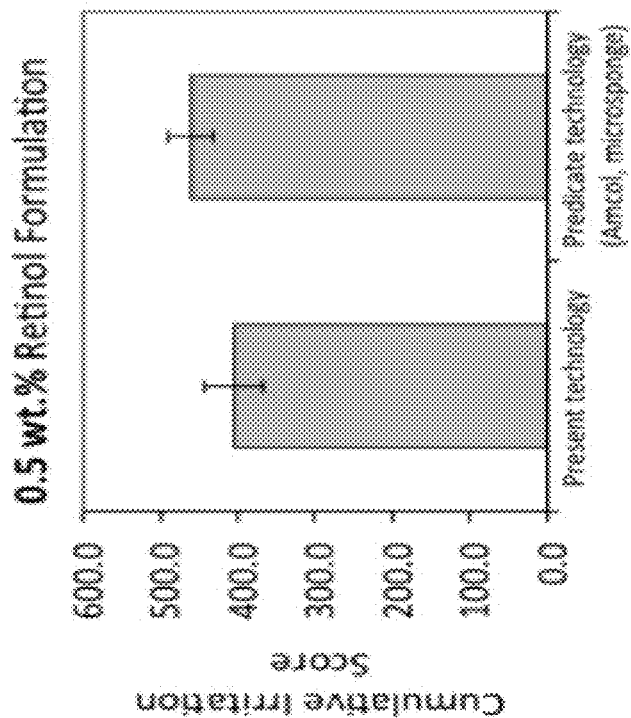
FIG. 10B is a bar graph showing cumulative irritation scores of a 0.2 wt % retinol formulation prepared as described in Example 4 throughout a three-week occlusive patch test as compared to identical formulations containing a predicate microencapsulation technology, the Microsponge by Amcol.
Figure 10A:
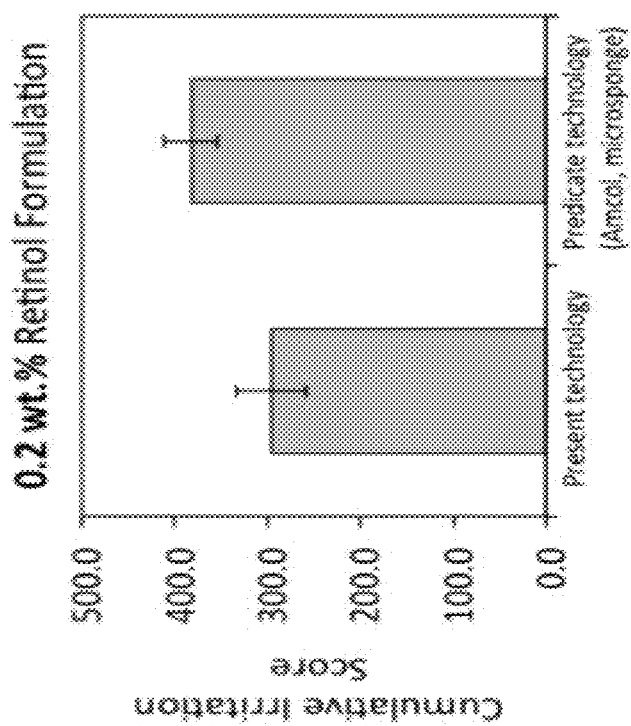
FIG. 10A is a bar graph showing cumulative irritation scores of a 0.2 wt % retinol formulation prepared as described in Example 4 throughout a three-week occlusive patch test as compared to identical formulations containing a predicate microencapsulation technology, the Microsponge by Amcol.

Example 3. Measuring the Stability of the Active Ingredient (FIG. 8)

Silicone particles were synthesized with encapsulated active ingredient. 1 mL aliquots of particles were made in multiple vials. Each aliquot was centrifuged to concentrate the particles into a loosely packed pellet. The supernatant was removed and replaced with deionized water. The new solution was thoroughly mixed. The amount of retinol in the particles was measured on "Day 0" using the SR method as described in Example 2.

Each vial was then sealed with parafilm and placed in a heat block at 45° C. for a maximum of two weeks. At different time points, Eppendorf tubes were removed. The SR method described above in Example 2 was employed to assess the amount of non-degraded retinol still within the particles. This result was compared against the known amount of retinol in the particles measured on "Day 0".

Example 4. Composition of a Formulation for Retinol-Encapsulated Silicone Particles (Formulated by EnDev Laboratories)

Retinol 0.50 wt. % loading
Example Ingredient List (by mass)
C13-14 Isoparaffin (1.00%-5.00%)
Dicaprylyl Carbonate (3.00%)
Particles with Encapsulated Retinol (5.00%) [Dried Powder]
Ethoxydiglycol (25.00%)
Ethylhexylglycerin (<1.00%)
Laureth-7 (1.00%-5.00%)
Pentylene Glycol (3.00%)
Phenoxyethanol (<1.00%)
Polyacrylamide (10.00%-20.00%)
Purified Water (58.00%)

Example 5. Method for Measuring Skin Irritation of a Formulation Containing the Particles with Encapsulated Retinol (Performed by AMA Labs) (FIGS. 9A, 9B, 10A and 10B)

Subject Selection

Twenty healthy male and female subjects 18 years old or older were selected based inclusion on exclusion criteria. Female subjects were not pregnant or lactating. For inclusion in the study, individuals were not currently under a doctor's care and free of any dermatological or systemic disorder including chronic skin allergies, which would interfere with the results, at the discretion of the investigator. The individuals were free of any history of acute or chronic disease that might interfere with or increase the risk associated with study participation. The individuals avoided direct sun exposure of the test site area and avoided the use of tanning beds for the duration of the study. The individuals were not currently taking any topical or systemic medication that may mask or interfere with the test results. None of the individuals had less than a two-week rest period since completion of any previous patch test.

Procedure

Subjects bathed or washed as usual. Approximately 0.2 mL or 0.2 g of the test material was dispensed onto an occlusive, hypoallergenic patch (Park-Davis Readi—Bandage or the equivalent). The patch was applied directly to the skin of the infrascapular regions of the back to the right or left of the midline. The test area was not to wetted or exposed to direct sunlight. Patches were removed 24 hours after each application. Prior to each reapplication, a technician evaluated test sites.

Skin response was evaluated according to the following scale:
  0=no evidence of any effect
  ?=minimal, uniform or spotty erythema 1=pink uniform erythema covering most or all of the contact site 2=pink-red erythema visibly uniform in entire contact site 3=bright red erythema with or without petechiae or papules 4=deep red erythema with or without vesiculation or weeping Evaluators were required to take and pass a visual discrimination examination conducted by a Board Certified Ophthalmologist using the Farnsworth-Munsell 100 Hue Test as published which determines a person's ability to discern color against a black background. The test was additionally modified to include a flesh tone background more nearly approaching actual use conditions, wherein erythematous skin is graded according to intensity.

The test material was applied five days weekly for 20 days to the same site, or until irritation scores of 3 or 4 were observed. If a reaction of 3 or 4 was observed, application of the test sample was discontinued and the score was recorded for the balance of the 21-day test. The maximum potential score for a test material was calculated by multiplying the maximum potential score (4) by the number of panelists completing the study by the number of days of evaluation (15). In the event of an adverse reaction, the area of erythema and edema was measured. The edema was estimated by the evaluation of the skin with respect to the contour of the unaffected normal skin. Accompanying edema at any test site was recorded with an "e" and described as mild, moderate or severe as compared with the normal surface of surrounding skin.

Figure 11B:
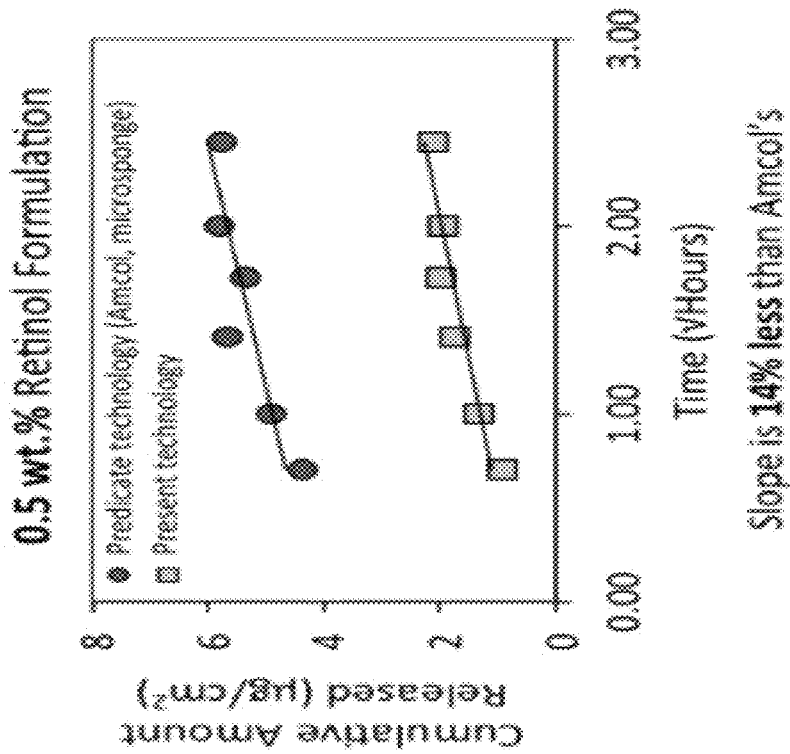
FIG. 11B shows in vitro release testing (IVRT) of a 0.5 wt % retinol formulation through a 0.2 μm nylon filter as compared to identical formulations containing a predicate microencapsulation technology, the Microsponge by Amcol.
Figure 11A:
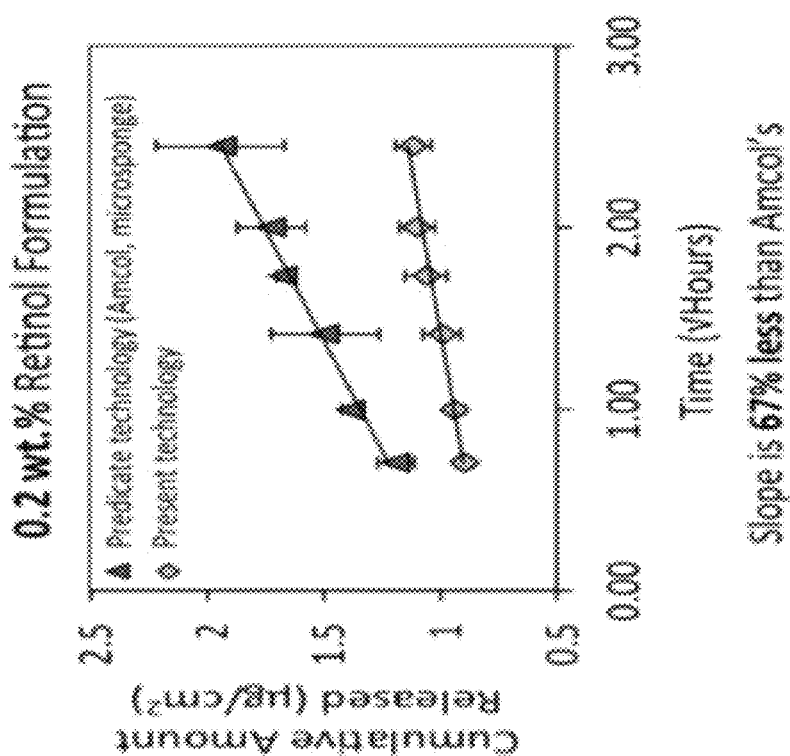
FIG. 11A shows in vitro release testing (IVRT) of a 0.2 wt % retinol through a 0.2 μm nylon filter as compared to identical formulations containing a predicate microencapsulation technology, the Microsponge by Amcol.

Example 6. Method for In Vitro Release Testing (IVRT) (Performed by Tergus Pharma) (FIGS. 11A and 11B)

Materials and Equipment:

The High Performance Liquid Chromatography (HPLC) System used was a LC-24 Shimadzu System including LC-20AD pump, CBM-20A Communications Bus Module, SIL-20AC$_{HT}$ Auto Injector, SPD-M20A Diode Array Detector, DGU-20A$_{3R}$ degasser and Empower 3 Software. The HPLC column used was an Agilent Zorbax Eclipse XDB C18 4.6 mm×50 mm 3.5 µm. The vertical diffusion cells were RR3 C1-C9, RR4 C1-C6 Crown or Allen Scientific Glass vertical diffusion cells. The individual volume of each cell was used to calculate sample results. The receiving chamber volume was approximately 14 mL. A glass donor chamber was placed over each membrane to define a 2.064 cm$^2$ application surface area during every test. The heater/circulators were HC-16 Lauda E 100. The IVRT membranes were Sterlitech Nylon Membranes, 0.45 µm, 47 mm cut to 32 mm, Lot 7007637.

Preparation of Solutions:

I. Receiving Media 65:35 Water: Methanol

For each liter of receiving media: With a 100 mL volumetric pipette 600 mL of water was added to a 1 L bottle. With a 50 mL volumetric pipette, 50 mL of water was added once to the bottle. With a 100 mL volumetric pipette 300 mL of acetonitrile was added to the bottle. With a 50 mL volumetric pipette 50 mL of acetonitrile was added once to the bottle. The contents of the bottle were mixed well and degassed prior to use.

II. 0.1% Formic Acid in Water

For each liter of mobile phase: 1 L of water was added to a 1 L bottle and 1 mL of formic acid was added to the bottle. The contents of the bottle were mixed well and degassed prior to use.

III. 0.1% Formic Acid in Acetonitrile

For each liter of mobile phase: 1 L of acetonitrile was added to a 1 L bottle and 1 mL of formic acid was added to the bottle. The contents of the bottle were mixed well and degassed prior to use.

When possible HPLC grade solvents and reagents were used.

IVRT Method Conditions:

Apparatus: Three vertical diffusion cells per sample per run

Surface Area: 1.767 cm$^2$

Sampling Intervals: 0.5, 1, 2, 3, 4, 5 and 6 hrs

Temperature: 32° C.±0.5° C.

Application Method: Wet mount

Application Amount: About 0.4 g, not weighed*

Sample Aliquot: 200 µL

Membrane: Sterlitech, Nylon 0.45 µm, 47 mm cut to 35 mm

Receiving Medium: 65:35 water:methanol

Receptor Volume: Approximately 14-16 mL

Stirring Speed: 600 rpm

*Sufficient test materials were applied to the membrane covering the surface area defined by the donor chamber such that no part of the membrane was exposed and an infinite dose was applied throughout the test period. In this case, about 400 mg of material was sufficient.

HPLC Method Conditions:

Mobile Phase A: 0.1% formic acid in water

Mobile Phase B: 0.1% formic acid in acetonitrile

Column: Agilent Zorbax Eclipse XDB C18 4.6 mm×50 mm 3.5 µm

Guard Column: NA

Column Temperature: 40° C.

Injection Volume: 80 µL

Detection Wavelength: 190-800 nm, 325 nm extracted

Run Time: 5 min, gradient

Flow Rate: 1.0 mL/min

Approximate retention time: 2.8 min

Auto-sampler temperature: 5° C.

Gradient Profile:

| Minutes | % A | % B |
| --- | --- | --- |
| 0.00 | 22 | 80 |
| 3.50 | 5 | 95 |
| 3.51 | 20 | 80 |
| 5.0 | 20 | 80 |

Study Procedures:

Receiving media was degassed and pre-warmed in a water bath. Stir bars were placed into the Franz cells and receiving media was then allowed to equilibrate in the cells to reach a temperature of 32±0.5° C. Membranes were placed over the Franz cells. A 15 mm wafer was placed on top of the membranes, and approximately 400 mg of formulation was spread evenly to cover the entire opening of the substrate. Three cells of each formulation were dosed. A glass disk was placed on top of each wafer covering the sample, then a glass donor chamber was placed on top of the glass disk, and the whole apparatus was secured in place with a clamp. The sampling arms of the cells were occluded with plastic wrap to prevent evaporation. Then 200 µL samples were removed with a pipette at the time points indicated above (in the gradient profile table) and receiving media was replaced in the cells after each pull. Samples were analyzed by HPLC.

Example 7. Protocol for Synthesizing Approximately 30 g of Silicone Particles made from TMOMS Monomers with 10 wt. % Retinol The following steps were conducted in a yellow room to protect retinol from degradation.

Preparation of Retinol Aliquots:
Step 1. 1.5 g all-trans crystalline retinol was weighed and placed in each of two 50 mL conical tubes.
Step 3. 42.413 mL ethanol was added to each conical tube and vortexed vigorously until all retinol was dissolved.
Step 4. 100 mg of BHT was weighed into two separate Eppendorf tubes and 1.25 mL of acetone was added to each Eppendorf and vortexed vigorously until all BHT was dissolved.

Preparation of Particles
Step 1. 283 mL of Mili-Q $H_2O$ was added to two separate 1 L glass beakers.
Step 2. 52 µL of 37% hydrochloric acid (HCl) was added directly to each glass beaker and fully mixed.
Step 3. 28.275 mL trimethoxymethylsilane (TMOMS) was added directly to each solution.
Step 4. Using a 2" stir bar coated with aluminum foil, both solutions were stirred at 350 rpm for 1.5 hrs.
Step 5. While still stirring, an additional 283 mL of Mili-Q $H_2O$ added directly to each solution.
Step 6. While still stirring, 424 µL triethylamine (TEA) was added directly to each solution to initiate the polycondensation step.
Step 7. After 3-5 min of polycondensation, one of the retinol solutions and one of the BHT solutions was added to each solution.
Step 8. Stirring of both solutions continued for 18-20 min total (from addition of TEA).

Drying the Particles:
Step 1. Each solution was carefully poured into two separate 1 L vacuum filters (4 filters total).
Step 2. The tops of the filter containers were air-sealed with saran wrap.
Step 3. Nitrogen gas was added to the top compartment of the vacuum containers, which were then sealed with saran wrap.
Step 4. A vacuum was applied to the filters for 45 min (or until cake layer is completely dry).
Step 5. A cake layer was removed with non-sharp-pointed tweezers, broken into pellets and added to four separate scintillation vials.
Step 6. The headspace of all 4 vials was filled with nitrogen gas.
Step 7. The pellet was milled into an ultrafine powder.
Step 8. The containers were closed and stored directly in −80° C. freezer.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

The present disclosures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method for making silicone particles with narrow size distributions and tunable degrees of crosslinking for encapsulation of an active ingredient in a matrix of the particles for controlled release of the active ingredient, the method comprising the steps of:
   agitating at least one type of silane monomer having two, three or four siloxane bonds in an acidic aqueous solution under conditions sufficient to allow for hydrolysis of the monomers;
   adding to the acidic aqueous solution a catalyst for forming polymers, gels and oligomers;
   preparing a second solution comprising a co-solvent and a hydrophobic active ingredient dissolved in the co-solvent;
   adding to the acidic aqueous solution the second solution of the active ingredient before or during silicone particle growth to form a combined solution, wherein the concentration of the co-solvent in the combined solution is at a minimum concentration necessary to allow precipitation of the active ingredient on and subsequently encapsulation in the growing silicone particles; and
   continuing to agitate the combined solutions to allow for a condensation reaction and formation of silicone particles with a size distribution wherein the diameter of the particles possess a coefficient of variance of 50% or less, the silicone particles encapsulating at least a portion of the active ingredient, wherein the tunable degree of crosslink density of the particles formed is based on the ratios of the monomers used.

2. The method as recited in claim 1, further comprising the step of removing a majority of the polymers, gels and large oligomers from the smaller hydrolyzed monomers and oligomers via centrifugation after the hydrolysis reaction and prior to the condensation reaction.

3. The method as recited in claim 1, wherein the at least one type of silane monomer comprises a conjugative group such that the group is available for covalent modification in or on the formed silicone particles.

4. The method as recited in claim 3, wherein the conjugative group comprises a vinyl, carboxylate, hydroxyl, epoxide, sulfhydryl, amide, acrylate, methacrylate, thiol or amine.

5. The method as recited in claim 1, wherein the at least one type of silane monomer having two siloxane bonds is selected from the group of dimethoxydimethylsilane (DMODMS), vinylmethyldimethoxysilane (VMDMOS), vinylmethyldiethoxysilane (VMDEOS) and/or 3-aminopropyl (diethoxy)methylsilane (AmDEOMS).

6. The method as recited in claim 1, wherein the at least one type of silane monomer having three siloxane bonds is selected from the group of trimethoxymethylsilane (TMOMS), vinyltrimethoxysilane (VTMOS), triethoxyvinylsilane (VTEOS), 3-aminopropyl trimethoxysilane (AmTMOS) and/or 3-(trimethoxysilyl) propylacrylate (AcTMOS).

7. The method as recited in claim 1, wherein the at least one type of silane monomer having four siloxane bonds is selected from the group of tetraethylorthosilicate (TEOS) and/or tetramethoxysilane (TMOS).

8. The method as recited in claim 1, wherein the at least one type of silane monomer is a ratio of a silane monomer having four siloxane bonds to a silane monomer having two siloxane bonds in the range of 1:1000 to 1:2.

9. The method as recited in claim 1, wherein the at least one type of silane monomer is a ratio of a silane monomer having three siloxane bonds to a silane monomer having two siloxane bonds in the range of 1:1000 to 1000:1.

10. The method as recited in claim 1, wherein the at least one type of silane monomer is a ratio of a silane monomer having four siloxane bonds to a silane monomer having three siloxane bonds in the range of 1:1000 to 1:2.

11. The method as recited in claim 1, wherein the at least one type of silane monomer is a ratio of a silane monomer having four siloxane bonds to a silane monomer having three siloxane bonds to a silane monomer having two siloxane bonds in the range of 1:(1 to 1000):(1 to 1000).

12. The method as recited in claim 1, wherein the catalyst is triethylamine or ammonium hydroxide.

13. The method as recited claim 1, wherein the particles range in size from about 100 nm to about 50 µm based on the concentration and types of silane monomers in the acidic aqueous solution and the stir speed during the polycondnesation step of the reaction.

14. The method as recited in claim 1, wherein the active ingredient is selected from retinol, retinylacetate, retinylpalmitate, alpha-tocopherol, tocopherolacetate, tocopheryl linoleate, tocopheryl nicotinate, linoleic acid, coenzyme Q-10, resveratrol, plant extracts/essential oils, ursolic acid, oleanolic acid, oil-soluble licorice, lipoic acid, desonide, clobetasol proprionate, betamethasone diproprionate, halobetasol proprionate, fluocinonide, ketoconazole, fluconazole, itraconazole, miconazole, clotrimazole, amphotericin, tretinoin, tazarotene, benzoyl peroxide, salicylic acid, pimecrolimus, mometasone furoate, fluocinolone acetonide, diflorasone diacetate, ingenol mebutate and combinations thereof.

15. The method as recited as in claim 1, wherein the co-solvent is an organic solvent.

16. A method as recited in claim 1, further comprising the step of adding an antioxidant to the combined solution to allow for the silicone particles encapsulating at least a portion of the antioxidant.

17. A method as recited in claim 16, wherein the antioxidant is butylated hydroxytoluene (BHT).

* * * * *

UNITED STATES PATENT AND TRADEMARK OFFICE
CERTIFICATE OF CORRECTION

PATENT NO. : 10,238,586 B2
APPLICATION NO. : 15/492786
DATED : March 26, 2019
INVENTOR(S) : Charles W. Shields, IV et al.

It is certified that error appears in the above-identified patent and that said Letters Patent is hereby corrected as shown below:

On the Title Page

Delete "(63) Continuation of application No. 62/325,117, filed on Apr. 20, 2016." under Related U.S. Application Data and replace with --(60) Provisional application No. 62/325,117, filed on Apr. 20, 2016.--.

Signed and Sealed this
Seventh Day of May, 2019

Andrei Iancu
*Director of the United States Patent and Trademark Office*